US006277772B1

(12) United States Patent
Gancet et al.

(10) Patent No.: US 6,277,772 B1
(45) Date of Patent: Aug. 21, 2001

(54) SUPERABSORBENT COMPOSITION FOR HYGIENE ARTICLES FREE FROM UNPLEASANT SMELLS

(75) Inventors: Christian Gancet; Serge Nicolas, both of Lons; Yves Taupin, Paris, all of (FR)

(73) Assignee: Ceca S.A., Puteaux (FR)

( * ) Notice: Subject to any disclaimer, the term of this patent is extended or adjusted under 35 U.S.C. 154(b) by 0 days.

(21) Appl. No.: 09/308,292

(22) PCT Filed: Nov. 6, 1997

(86) PCT No.: PCT/FR97/01990

§ 371 Date: Aug. 16, 1999

§ 102(e) Date: Aug. 16, 1999

(87) PCT Pub. No.: WO98/20915

PCT Pub. Date: May 22, 1998

(30) Foreign Application Priority Data

Nov. 13, 1996 (FR) .................................................. 96 13813

(51) Int. Cl.⁷ ............................ D04H 1/00; D04H 13/00; D04H 3/00; D04H 5/00
(52) U.S. Cl. .......................... 442/327; 428/327; 428/328; 428/330
(58) Field of Search ..................................... 442/327, 328, 442/330

(56) References Cited

U.S. PATENT DOCUMENTS

| 4,525,410 | * | 6/1985 | Hagiwara et al. | .................... 428/198 |
| 5,951,534 | * | 9/1999 | Cummings et al. | .................. 604/359 |
| 5,997,690 | * | 12/1999 | Woodrum | .............................. 162/100 |
| 6,096,299 | * | 8/2000 | Guarracino et al. | ................. 424/76.1 |

FOREIGN PATENT DOCUMENTS

| 3816352 | 5/1988 | (DE) . |
| 389015 | 2/1990 | (EP) . |
| EPO 0103214 | 8/1983 | (JP) . |
| 63-156540 | 6/1988 | (JP) . |
| WO 91/12029 | 8/1991 | (WO) . |
| WO 94/22501 | 10/1994 | (WO) . |
| WO 95/24173 | 9/1995 | (WO) . |
| WO 95/26207 | 10/1995 | (WO) . |
| WO 91/12031 | 8/1999 | (WO) . |

* cited by examiner

Primary Examiner—Blaine Copenheaver
Assistant Examiner—Norca L. Torres
(74) Attorney, Agent, or Firm—Smith, Gambrell & Russell, LLP

(57) ABSTRACT

The invention concerns a superabsorbent composition containing a superabsorbent polymer powder, for instance polyacrylic and a zeolite powder exchanged with metal cations with bactericidal properties, in particular with silver ions. The hygiene articles incorporating them do not give off nor develop unpleasant smells though soaked with corporeal liquids.

17 Claims, No Drawings

SUPERABSORBENT COMPOSITION FOR HYGIENE ARTICLES FREE FROM UNPLEASANT SMELLS

TECHNICAL AREA

The present invention concerns the utilization of bactericidal zeolites containing metal ions to confer antiodor properties onto superabsorbent hydrophilic polymers.

The superabsorbent polymers (SAP) are used in the manufacture of disposable pants to improve their absorption capacity for liquids, in particular, for urine. When the absorbent article is impregnated with urine, it develops various strong and unpleasant odors, including the odor of ammonia, coming from the hydrolysis of urea by bacterial ureases (Proteus, Acinetobacter, etc.) present in the skin and in the digestive tract.

Search for a solution to the problem of odors is especially pressing because, in our days, the absorption capacity of articles for protection against body fluids has been increasing very significantly by incorporating in them superabsorbent polymers (SAP), in particular, hydrophilic polymers and copolymers of acrylic acid; at the same time, the duration of keeping them in place is increased and all these conditions promote the development of microbial and enzymatic activity and emission of odors which result from that.

PRIOR ART

With the purpose of eliminating these odors, numerous actions were undertaken in the field of hygiene in general; this was done in different ways. For example, odor or ammonia absorbents have been widely used (U.S. Pat. No. 3,340,875 of the Scolt [sic, this is a typo in French text, should be Scott] Paper Company, U.S. Pat. Nos. 4,795,482 and 4,826,497 of Union Carbide) in combination with deodorants, fragrances, etc. The use of oxidizing agents (hydrogen peroxide, chlorine dioxide) as well as bactericides (in particular, quaternary ammonium salts), antibiotics, complexing agents, surfactants, alone or in combinations of these, have also been recommended. These products pose the general problem that they have an irritating action on the skin and the mucosa. The absorbents for odors or ammonia are certainly less dangerous in this regard, but they leave a clear field for bacterial proliferation which remains bothersome and which should be controlled to start with.

DESCRIPTION OF THE INVENTION

Now it was found that it is possible to formulate superabsorbent polymers with zeolite exchanged with metal ions in order to produce absorbent compositions, which, when they are saturated with urine or biological fluids, and are maintained under the conditions of utilization which are propitious for development of bacteria, do not give rise either to large evolution of ammonia or to the emission of repulsive or simply unpleasant odors and which impart this property to the hygiene articles that contain them.

Thus, the invention consists of a superabsorbent composition intended for the production of hygiene articles of the type of pants, diapers, do not develop unpleasant odors, comprising a superabsorbent polymer for water, saline solutions and body fluids and a zeolite exchanged with metal cations having bactericidal properties in the proportion of 0.05% to 10%, preferably 0.01 to 5% with respect to the superabsorbent composition.

Superabsorbent polymers are products which respond to the definition of superabsorbents as it is found in the work "Absorbent Polymer Technology", "Studies in Polymer Sciences 8, Elsevier 1990", that is, dry materials which can absorb spontaneously an aqueous fluid at a rate of at least twenty times its own weight. The superabsorbent polymers in the sense of the present invention are polymers which are obtained by the polymerization of water-soluble, ethylenically unsaturated monomers with partial crosslinking, in particular, acrylic acid and methacrylic acid, as well as their alkali salts, which are obtained by a method of polymerization in solution or in suspension. These polymers have a very large capacity of absorption and retention of water and aqueous solutions and today are widely used in the market in the form of powders, the particle sizes being between 100 and 800 µm. The literature on them is very rich; one can consult, for example, EP-A-0312952 (The Dow Chemical Company) and EP-A-0441507 (Sumitomo Seika Chem.).

Zeolites are microporous crystalline aluminosilicates, the structure of which is that of assemblies of tetrahedral groups of $SiO_4^-$ and $AlO_4^-$ and which can be represented by the formula expressed as oxides

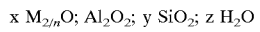

$$x\, M_{2/n}O;\ Al_2O_2;\ y\, SiO_2;\ z\, H_2O$$

in which M is an alkali or alkaline-earth cation with the valence n, x is a number less than or equal to 1, y is between 2 and 30, and z is a number which expresses the state of hydration of the zeolite.

The bactericidal properties of zeolites exchanged with certain metal cations, which themselves have bactericidal properties, are known. They have been used to prepare bactericidal fibers that permit the manufacture of articles of current consumption: socks, undergarments, etc., especially in Japan (U.S. Pat. Nos. 4,525,410 and 5,064,599, Kanebo). Recently, the Procter & Gamble Company claimed an absorbent system that controls body odors by incorporating into them zeolites exchanged with silver in the perforated plastic film which envelopes the absorbent (WO 95/24173). Others place a layer of such zeolites in the sandwich manner between two sheets of superabsorbent polymer films (JP 63 156540, Dainippon Printing Co.). Other patents describe the aqueous dispersion of zeolites exchanged with silver in textile layers (JP 63 097,159, Matsui), or they are used by them impregnating confetti dispersed in the absorbent components of hygiene articles (EP 0389015, Procter & Gamble). If one excepts the very curious synergism between a metal zeolite and a ceramic which radiates in the far infrared (JO63-210174, OTA), one does not find any teaching published about compositions containing a superabsorbent polymer and a metal zeolite.

The superabsorbent compositions of the invention are prepared very easily, these being compositions which resist the emission of ammonia and unpleasant odors when they are saturated with body fluids, for example, a mixture of superabsorbent polymer powder with a particle size between 100 and 800 µm with a zeolite powder exchanged with metal cations, preferably having a particle size between 0.5 and 20 pm, at a rate of 0.05 to 10% and preferably 0.1 to 5% by weight of the exchanged zeolite with respect to the composition.

These exchanged zeolites are themselves prepared in the known manner starting from natural or synthetic zeolites. More particularly, zeolites A (LTA) or faujasites (FAU) or their mixtures are used for this purpose. The zeolite powder is suspended in water under agitation and then an aqueous solution of the metal ion with bactericidal properties, in particular, the $Ag^+$, $Cu^{2+}$, $Zn^{2+}$ ions, is added to it. It is recommended to disperse the zeolite powder to be exchanged preferably at pH 7–8 to avoid the precipitation of the metal oxide or hydroxide. The useful quantity of $Ag^+$ ions attached to the zeolite is between 0.01 and 10% by weight with respect to the zeolite, preferably between 0.05% and 5%. The quantity of $Cu^{2+}$ and $Zn^{2+}$ ions is between 0.1 and 25%, preferably between 0.2 and 15% by weight.

The superabsorbent compositions of the invention gel upon contact with water, aqueous saline solutions or body fluids as the superabsorbents of the prior art, and the gels thus formed behave essentially identically. Thus, one can use them instead of the ordinary superabsorbents in the manufacture of hygiene articles, such as disposable diapers, or disposable pants for babies, children, adults or the elderly of both sexes.

Not suffering from any contraindication, the zeolites exchanged with the metal ions $Ag^+$, $Cu^{2+}$ and $Zn^{2+}$ be justly considered as being harmless, on the one hand, because these ions are strongly attached to the inside of the zeolite structure, and, on the other hand, because these ions are traditionally and widely used in antiseptic compositions for the skin (Flanamazinc® and Sicazine® 1%; 1% silver sulfadiazine with a silver content of 0.3%, Dermocuivre®; copper sulfate at 0.2%, zinc oxide at 10%). The hygiene articles, such as disposable diapers and disposable pants for babies and young children, adults or elderly of both sexes, containing these compositions, are also the objects of the present invention.

The evaluation of the real efficacy of the antiodor products is a delicate matter. However, in a context of bacterial inhibitors to prevent the decomposition of urea into ammonia, one can estimate the efficacy of the products of the invention, on the one hand, by their ability to limit or even eliminate bacterial development, and, on the other hand, by the evolution of ammonia in the presence of various substances with which they are associated in the production of diapers and other sanitary articles, in particular, superabsorbent polymers. The efficacy of these products is quantified here by counting the microorganism colonies per unit volume (cfu/mL, standing for colony-forming units). However, one must also decide on the global results satisfied by the olfactory tests under conditions which simulate acceptably the conditions of utilization of the products in which the superabsorbent composition, presumed to inhibit odors, is incorporated. These are carried out by saturating a diaper with urine under standardized inoculation conditions and then holding all this at a mild temperature and subjecting the object to an odor-testing panel to give a global evaluation of any bad odors. These tests are described in the examples given below which illustrate the unexpected efficacy of the products according to the invention. In these tests, the superabsorbent polymer used is a partially neutralized polyacrylic acid marketed under the name of AQUA-KEEP®D (Elf Atochem S.A.).

EXAMPLES

Example 1

Preparation of Zeolites Exchanged with Silver

Zeolite X (SILIPORITE® G5 by CECA S.A.), 100 g, counted as anhydrous equivalent, is suspended in 300 cm$^3$ of water. The pH of the suspension is lowered from 10.5 to 7 by adding 18 cm$^3$ of 2 N nitric acid. Then, 50 cm$^3$ of a 0.188 molar silver nitrate solution is added to the suspension. The suspension is then agitated at ambient temperature for 3 hours. The zeolite thus exchanged with silver is dried at 100° C. for 2 hours and then ground with the aid of a RETSCH turbine grinder equipped with a 0.08 mm grid. The sizes of the zeolite particles range from 0.5 to 20 µm. Under these exchange conditions, almost the entire amount of silver used is exchanged in the zeolite structure. As a matter of fact, only traces of silver are detected in the mother liquors and in the washing waters. The zeolite exchanged with silver thus contains 1.0% by weight of silver.

In the same way, zeolites X exchanged with 0.5 and 0.2% by weight of silver, are produced by dividing the molarity of the silver nitrate solution by 2 and 5, respectively.

Example 2

Odor-inhibiting Effect and Proliferation of Bacteria
Collection of Urine

The test can be carried out either on a real pooled urine sample or on synthetic urine prepared at the time of use having the following composition:

| For 1 L of water: | |
| --- | --- |
| urea | 25 g |
| NaCl | 9 g |
| $K_2SO_4$ | 4 g |
| $(NH_4)_2SO_4$ | 2.5 g |
| $MgSO_4$ | 0.6 g |
| glucose | 5 g |
| $Ca(OCOCH_3)_2$ | 0.7 g |
| yeast extract | 5 g |

Preparation of the Inoculum

The inoculum is prepared with 20 mL of real or synthetic urine, 0.5 g of urea and either with 2 g of soiled fluff (already having an ammonia odor) or with a chosen bacterial strain. The mixture is incubated for 2 days, during which the collected urine is stored at 4° C.

At the time of the test, the inoculum has a marked odor which is a sign of satisfactory growth. In the isolated strains, the bacterial concentration was measured and expressed in cfu/mL, in order to provide reproducible inoculation.

Preparation of the Samples

Eight hermetically sealed polyethylene boxes are prepared for each product to be tested. In each box, a 6 cm×7.5 cm square of cellulose (fluff) tampon weighing approximately 3 g is deposited, these containing approximately 0.75 g of superabsorbent dispersed in the mass, with the antiodor products to be tested added or not added.

Then, 30 mL of real or synthetic urine inoculated at a rate of 10$^4$ cfu/mL is poured onto each square. The boxes are closed and incubated overnight in an oven at 37° C.

Evaluation of the Odor

At the time of the test, the boxes are taken out from the oven and presented randomly to the persons of the jury who must grade the odor between 0 and 5. The absence of NH$_3$ odor is graded 0 and a very strong odor is graded 5. For each of the products tested, the mean of the grades obtained is calculated. The results are summarized in the table given below.

Counting of the Bacteria

After evaluation of the odor, the microorganisms are counted in each type of sample. In order to do this, the samples are diluted with 70 mL of sterile water and the counting is carried out with the aid of a Millipore plate. The result is expressed in cfu/mL.

Results

The control is carried out with the ordinary superabsorbent, Aqua-Keep®D (SAP). The superabsorbents of the invention are compositions of Aqua-Keep D/zeolite X-Ag (SAP/X-Ag) in variable quantities and Ag levels. The following table gives the grades of the panel (grade 0 to 5) and the bacterial count (cfu/mL).

| SAP | grade | counting |
|---|---|---|
| SAP control | 3.6 | 3000 |
| SAP + 1% X-Ag with 1% Ag | 3.5 | 0 |
| SAP + 0.1% of X-Ag with 1% Ag | 3.1 | 0 |
| SAP + 1% X-Ag with 0.2% Ag | 2.5 | 200 |

What is claimed is:

1. A superabsorbent composition for the production of a hygiene article including underwear, pants or a diaper, which, when saturated with body fluids, does not give rise to the emission or development of unpleasant odors, said composition comprising:
   i) a superabsorbent polymer powder having a particle size between 100 and 800 $\mu$m, and
   ii) a zeolite powder comprising zeolite A (LTA), faujasite (FAU), or a mixture thereof, said zeolite powder having a particle size between 0.5 and 20 $\mu$m and exchanged with cations having bactericidal properties, said cations selected from the group consisting of cations of silver, copper, zinc, and a mixture thereof.

2. The composition according to claim 1 wherein the metal cations with bactericidal properties are silver in a proportion of 0.01–10 wt % of the zeolite.

3. The composition according to claim 1, wherein the metal cations with bactericidal properties are silver in a proportion of 0.05–5 wt % of the zeolite.

4. The composition according to claim 1, wherein the metal cations with bactericidal properties are copper or zinc in a proportion of 0.1–25 wt % of the zeolite.

5. The composition according to claim 1, wherein the metal cations with bactericidal properties are copper or zinc in a proportion of 0.2–15 wt % of the zeolite.

6. The composition according to claim 1, wherein the exchanged zeolite powder is in a proportion of 0.05–10 wt % of the superabsorbent composition.

7. The composition according to claim 1, wherein the exchanged zeolite powder is in a proportion of 0.1–5 wt % of the superabsorbent composition.

8. A hygiene article containing the composition according to claim 1.

9. The hygiene article according to claim 8, wherein said article is a disposable diaper.

10. The hygiene article according to claim 9, wherein said article is a diaper for babies.

11. The hygiene article according to claim 9, wherein said article is a diaper for young children.

12. The hygiene article according to claim 9, wherein said article is a diaper for adults.

13. The hygiene article according to claim 8, wherein said article is disposable pants.

14. The hygiene article according to claim 13, wherein said article is disposable pants for babies.

15. The hygiene article according to claim 13, wherein said article is disposable pants for young children.

16. The hygiene article according to claim 13, wherein said article is disposable pants for adults.

17. The composition according to claim 1, wherein the zeolite powder comprises faujasite (FAU).

* * * * *